US009364575B2

(12) United States Patent
Habbel (10) Patent No.: US 9,364,575 B2
(45) Date of Patent: Jun. 14, 2016

(54) AROMA SCENT DISPERSER ASSEMBLY (71) Applicant: Sam Habbel, Scottsdale, AZ (US)

(72) Inventor: Sam Habbel, Scottsdale, AZ (US)

( * ) Notice: Subject to any disclaimer, the term of this patent is extended or adjusted under 35 U.S.C. 154(b) by 129 days.

(21) Appl. No.: 13/999,834

(22) Filed: Mar. 27, 2014

(65) Prior Publication Data
US 2015/0273099 A1     Oct. 1, 2015

(51) Int. Cl.
*A61L 9/12*     (2006.01)
(52) U.S. Cl.
CPC .............. *A61L 9/122* (2013.01); *A61L 2209/11* (2013.01); *A61L 2209/133* (2013.01)
(58) Field of Classification Search
CPC .................................. A61L 9/12; A61L 9/122
See application file for complete search history.

(56) References Cited

U.S. PATENT DOCUMENTS

| 3,923,934 | A |   | 12/1975 | Watkins |
|---|---|---|---|---|
| 4,059,422 | A |   | 11/1977 | Steiner |
| 4,523,870 | A | * | 6/1985 | Spector ..................... A61L 9/12 239/55 |
| 7,942,388 | B2 |   | 5/2011 | Sussa et al. |
| 8,196,902 | B1 |   | 6/2012 | Pystin |
| 2002/0158351 | A1 | * | 10/2002 | Wohrle ................... A61L 9/035 261/142 |
| 2009/0054116 | A1 |   | 2/2009 | Hakunti et al. |
| 2011/0449259 |   |   | 3/2011 | Beland et al. |
| 2012/0205460 | A1 |   | 8/2012 | Franks |

* cited by examiner

*Primary Examiner* — Sean E Conley
(74) *Attorney, Agent, or Firm* — Paul Bogdon (57) ABSTRACT

An aroma scent dispersing assembly which selectively meters the fragrance emittance output, varying the concentration of aroma vapor in the discharge air flow is disclosed. The dispersing assembly includes a house having interconnected base members, selectively removable cover, opposite side walls, front and end walls defining an inner compartment with at least the end wall having access openings therethrough. A motor driven forced air fan assembly is arranged in the compartment and includes controls for selectively generating a flow of air from the front wall to discharge through the access openings of the end wall. An aroma dispensing cartridge assembly is arranged in the compartment and has apertures therethrough to expose the interior to the flow of air. A scented vapor emitting source, such as one or more wafers is supported by the aroma dispensing cartridge and is exposed to the flow of air. The aroma dispensing cartridge assembly is constructed for being selectively movable to meter and vary the amount of exposure of the vapor emitting source to the flow of air.

18 Claims, 9 Drawing Sheets

| Fragrance Emmittance Output Adjustment ||||||| 
|---|---|---|---|---|---|---|
| Holder 1 | Holder 2 | Holder 3 | Holder4 | Holder 5 | Holder 6 | Output Level |
| Open | Open | Open | Open | Open | Open | Maximum |
| Halfway | Halfway | Halfway | Halfway | Halfway | Halfway | Medium |
| Closed | Closed | Closed | Closed | Closed | Closed | Minimum |
| Halfway | Closed | Closed | Closed | Closed | Closed | Level 1 |
| Open | Closed | Closed | Closed | Closed | Closed | Level 2 |
| Halfway | Halfway | Closed | Closed | Closed | Closed | Level 3 |
| Open | Open | Closed | Closed | Closed | Closed | Level 4 |
| Halfway | Halfway | Halfway | Closed | Closed | Closed | Level 5 |
| Halfway | Halfway | Halfway | Halfway | Closed | Closed | Level 6 |
| Open | Open | Open | Closed | Closed | Closed | Level 7 |
| Halfway | Halfway | Halfway | Halfway | Halfway | Closed | Level 8 |
| Open | Open | Open | Open | Closed | Closed | Level 9 |
| Open | Open | Open | Open | Open | Closed | Level 10 |

*Fig.16*

AROMA SCENT DISPERSER ASSEMBLY

BACKGROUND OF THE INVENTION

1. Field of the Invention

The invention relates to an aroma scent disperser assembly and particularly to one that selectiving meters the fragrance emittance output, that is varies the concentration of aroma vapor in the discharge air flow.

2. Description of the Prior Art

There are a vast number of different designs of aroma or fragrance dispensing or dispersing devices. Some of the dispersing device use forced air fans to move air over or through volatile scent sources such as liquid scent-filled cartridges, wick soaked liquid scents, discs of vaporizable scent emitters, solid wafers of volatile scent emitter substances, or porous pads impregnated with scent volatile liquid scent. Most of the aroma dispersing devices are intended to discharge air filled fragrant or savory scents being what is generally known as air fresheners. When using the term "aroma" herein it is not to be limited to pleasant smells but encompasses scents that function as insecticides, deodorants, as well as air fresheners or any other odor that serve to condition, modify or otherwise change the atmosphere.

Of the various type of aroma scent dispersing device, most use a single scented vapor emitting source and are on-off devices emitting a steady discharge of scented air during "on" operation. The Patent to Spector, U.S. Pat. No. 4,523,870 discloses a typical on-off aroma-dispersing cartridge and holder assembly for automobile which cooperates with the forced air ventilation system of the vehicle to diffuse an aromatic vapor into the forced air stream whereby the aromatically-charged interior atmosphere is continuously maintained as long as the assembly is in its active state and the ventilation system is operating. The Patent to Suissa, et al, U.S. Pat. No. 7,942,388 discloses a scent diffusion device that includes an air flow generator for forcing air through a scent diffusion module or cartridge filled with material drenched scent emitters. The device includes several scent diffusion modules which may be positioned completely in or completely out of the air flow stream. The Suissa, et al device permits the ready replacing of the cartridges after they are dried out and not to expose multiple modules at the same time but to replace a scent emitter filled cartridge when one dries out from use. The Suissa, et al scent diffusion device is a typical on-off device. The Patent to Steiner, U.S. Pat. No. 4,059,422 discloses an on-off scent dispenser which uses a motor operated fan to pass an air stream over a scent emitter control agent. The Steiner device includes an air controller in the path of the air stream, the controller having two shiftable aperture members to provide maximum air flow or to block the air flow. Other on-off type scent disperser devices are disclosed in the Watkins Patent, U.S. Pat. No. 3,923,934; Beland, et al Patent Application, Publication No. US2011/0049259; and Franks Patent Application, Publication No. US2012/0205460.

Another typical on-off dispenser device which incorporates multiple cartridges for storing multiple and different fragrance is the vehicle mounted device of Pystin, U.S. Pat. No. 8,196,902, which includes a somewhat complicated control system for selecting one of different fragrance for distribution into the interior of the vehicle.

A drawback or problem in all of the known scent disperser devices is that none provide metering of scent concentration levels, a desirable feature. In many different environments where aroma scent emissions are needed, various concentrations of aroma distribution are most desirable. In some environments a strong emission concentration is called for and in others a mild concentration is appropriate. Different settings would call for differing emission concentrations between strong and mild. Another drawback or problem of known scent disperser devices is that they typically are constructed to be either wall mounted or set on horizontal surface such as a floor, counter top, table, or such like. In others words, they are mounted on a surface or positioned on a horizontal surface or a vertical surface, but not constructed for both. Where mounting on both surfaces is desirable, two or more separated devices would be required. In addition to the drawbacks and problems mentioned many of the known scent dispersing devices are intricate and complex in construction.

The present invention overcomes the drawbacks and problems inherent in existing known aroma scent dispersing devices, by providing a portable aroma scent dispersing device, which is simple in structure, combining relatively few parts, and which is capable of selectively and simply metering, varying, and regulating the amount of exposure and concentration of aromatic vapor to and in an air stream to be discharged into the environment of a room. The simple and uncomplicated construction of the aroma scent disperser device of the invention is also structured for selectively mounting on vertical surfaces such as a wall or horizontal surfaces such as ceilings or to be simply placed on floors, tables, counter tops, or the like. Achieving the most desirable feature of metering the scent concentration in the discharge airstream, the simple construction of the portable scent disperser device of this invention is capable of relatively low cost manufacture and readily affordable to the residential, business, or industrial consumer.

SUMMARY OF THE INVENTION

The present invention provides an aroma scent dispersing or dispensing assembly in which an aromatic vapor emitter source is selectively metered or regulated for exposing the amount of the same aromatic vapor emitting source to a forced air flow over and around the vapor emitting source to thereby regulate the concentration of the aromatic vapor in the air flow dispersed into the ambient surroundings. The aroma scent dispersing assembly includes a housing having interconnected base member selectively, removable cover, opposite side walls, front and end walls, the housing defining an inner compartment with at least the end wall defining access openings therethrough. Arranged within the compartment is a forced air source for selectively generating a flow of air from the front wall to the end wall and through the access openings to the ambient surroundings. An aroma dispersing cartridge is arranged in the housing compartment, the cartridge assembly defining apertures therethrough to expose the interior to the flow of air from forced air source. The cartridge assembly is sized and shaped for supporting a scented vapor emitting source, such as an aroma emitting wafer, but not limited thereto, the vapor emitting source being exposed to the flow of air. The cartridge assembly is further sized, shaped, and arranged for selectively metering or regulating the amount of exposure of the vapor emitting source to the flow of air to thereby regulating the concentration of the aromatic vapor dispersed into the ambient surroundings from the housing of the aroma scent dispensing assembly.

One form of the present aroma vapor dispensing assembly includes a housing having an elongated base member; a selectively removable upper disperser cover; spaced apart front and back walls each defining access openings; and spaced apart side walls joined with the front and back walls, and with the base member. An inner compartment is defined within the confines of the interconnected base member, front and back walls, and side walls. A motor driven forced air source is supported in the compartment by the front wall and includes a selectively operable variable speed control unit. The forced air sourced is arranged to generate a flow of air between the front end wall and through the access openings of the back end wall and through openings in the base member, if desired. A generally box-shaped aroma vapor dispensing cartridge assembly is arranged in the compartment for receiving and supporting a scented vapor emitting source, such as a wafer, which is exposed to the flow of air, the vapor dispensing cartridge being constructed for being selectively adjusted for metering, regulating or controlling the amount of exposure of the vapor emitting source to the flow of air. More specifically, the vapor dispensing cartridge assembly includes at least one open top holder supported by the base member including spaced front and back ends defining spaced end apertures and spaced sides defining side apertures, the end and side apertures arranged to be open to the flow of air. The vapor dispensing cartridge assembly further includes a generally box-shaped holster shaped and sized for supporting a scented vapor emitting sources such as a wafer slidably received within and supported by the holder, the holster having spaced side walls and spaced end walls each defining arrays of slots matching the front end and back end apertures and side apertures of the holder. The holster is selectively movable between aligning the slots and apertures to closing the slots from the apertures, whereby air will flow over the cartridge assembly, that is over the tops of the holder and holster, at all positions of the holder and holster and engage this interior of the holster and the vapor emitting source when the slots and apertures are open to each other and will bypass the interior of the holster when the apertures and slots are closed with respect to each other. The combination of the holder and the holster which is selectively slidable with respect to the holder will form what would be called a shutter for metering regulating, varying, or controlling the amount of exposures of scented vapor emitting source within the holster to the flow of air. The scent dispersing assembly could also include a chassis secured to the base member of the housing, the chassis shaped and sized for selectively removably supporting the aroma dispersing cartridge assembly, that is the holder and holster. In its preferred form, the present aroma scent dispersing assembly would include a plurality of aroma dispersing cartridge assemblies arranged spaced from one another within the compartment of the housing wherein adjacent cartridge assemblies are spaced generally parallel to each other. Either or both the base member and/or back wall may include removable attachment arrangements for selectively securing the aroma scent dispersing assembly on horizontal or vertical surfaces such as walls or ceilings. Without the base member attachments, the aroma scent dispersing assembly could be set on a floor, desk, table, or cabinet surface. The speed control for the motor driven forced air source or fan could also be arranged with a programmable timing means for selectively turning the motor driven fan on and off at desired times.

Various other advantages, details, and modification of the aroma scent dispersing assembly of the present invention will become apparent and indicated as the following description of a certain preferred embodiment and modifications thereof proceed.

BRIEF DESCRIPTION OF THE DRAWINGS

In the accompanying drawings, I show a certain preferred embodiment of my present invention in which.

DESCRIPTION OF PREFERRED EMBODIMENTS

Figure 1:
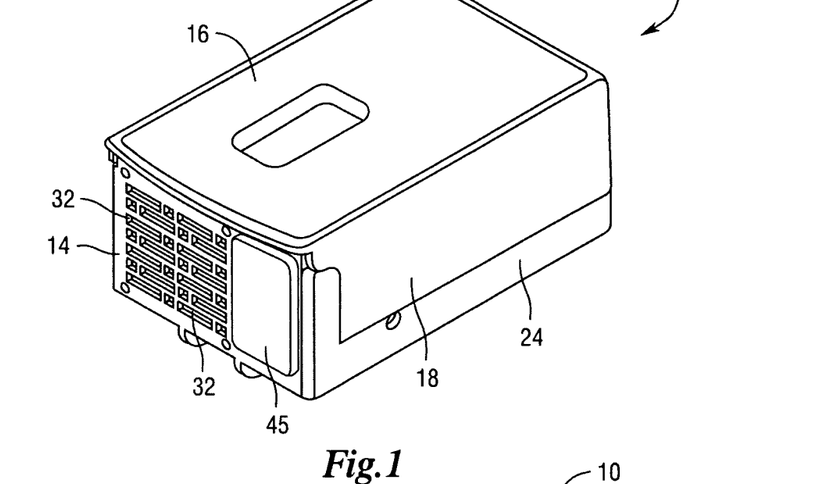
FIG. 1 is a perspective view of the aroma scent dispersing assembly of the present invention.
Figure 2:
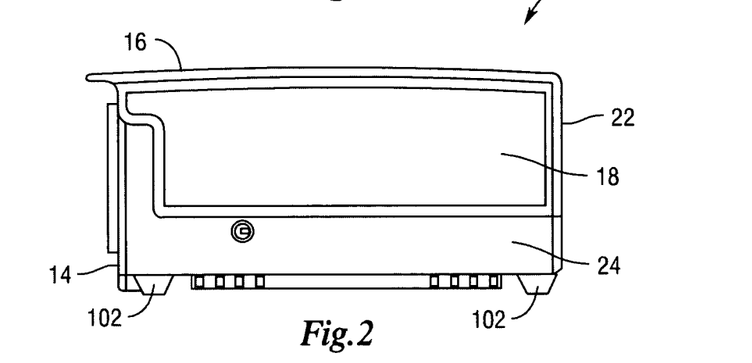
FIG. 2 is a side elevation view of the aroma scent dispersing assembly of FIG. 1.
Figure 2A:
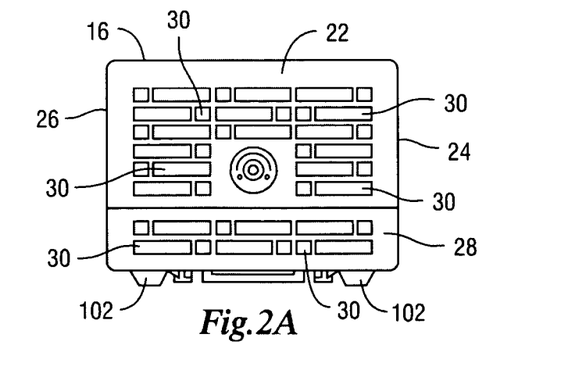
FIG. 2A is a rear end elevation view of the aroma scent dispersing assembly of FIG. 1.
Figure 3:
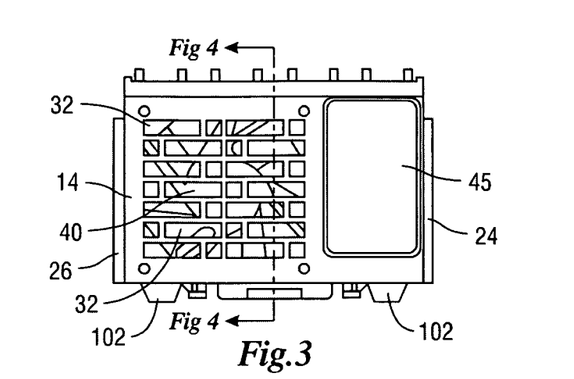
FIG. 3 is a front elevation view of the aroma scent dispersing assembly of FIG. 1 with the cover removed.

Referring now to the drawings there is shown an aroma scent dispersing assembly 10 which includes an elongated base member 12 defining an array of openings 13 therethrough, front end wall 14 secured to the base member 12 by suitable attachments. A detachable cover 16 having an elongated upper surface, downwardly expanding side flaps 18 and 20 and end section 22. With the cover 16 in place, the side flaps 18 and 20 meet with lower wall section 24 and 26 together forming side walls of the assembly 10. Also with the cover 16 in place, the end section 22 thereof meets with a lower end wall section 28 to form the rear end wall of the assembly 10. As shown clearly in FIG. 2A, the end section of cover 16 and lower end wall section 28 defines access openings 30, the openings 30 referred to hereafter as rear wall access openings 30. As clearly shown in FIGS. 1, 3, 5 and 8, front end wall 14 defines an array of generally parallel openings 32 therethrough. The interconnected base member 12, front end wall 14, side walls comprised of side flaps 18 and 20, and rear end wall comprised of end section of cover 16 and lower end wall section 28 define an inner compartment 34 of the assembly 10.

Figure 8:
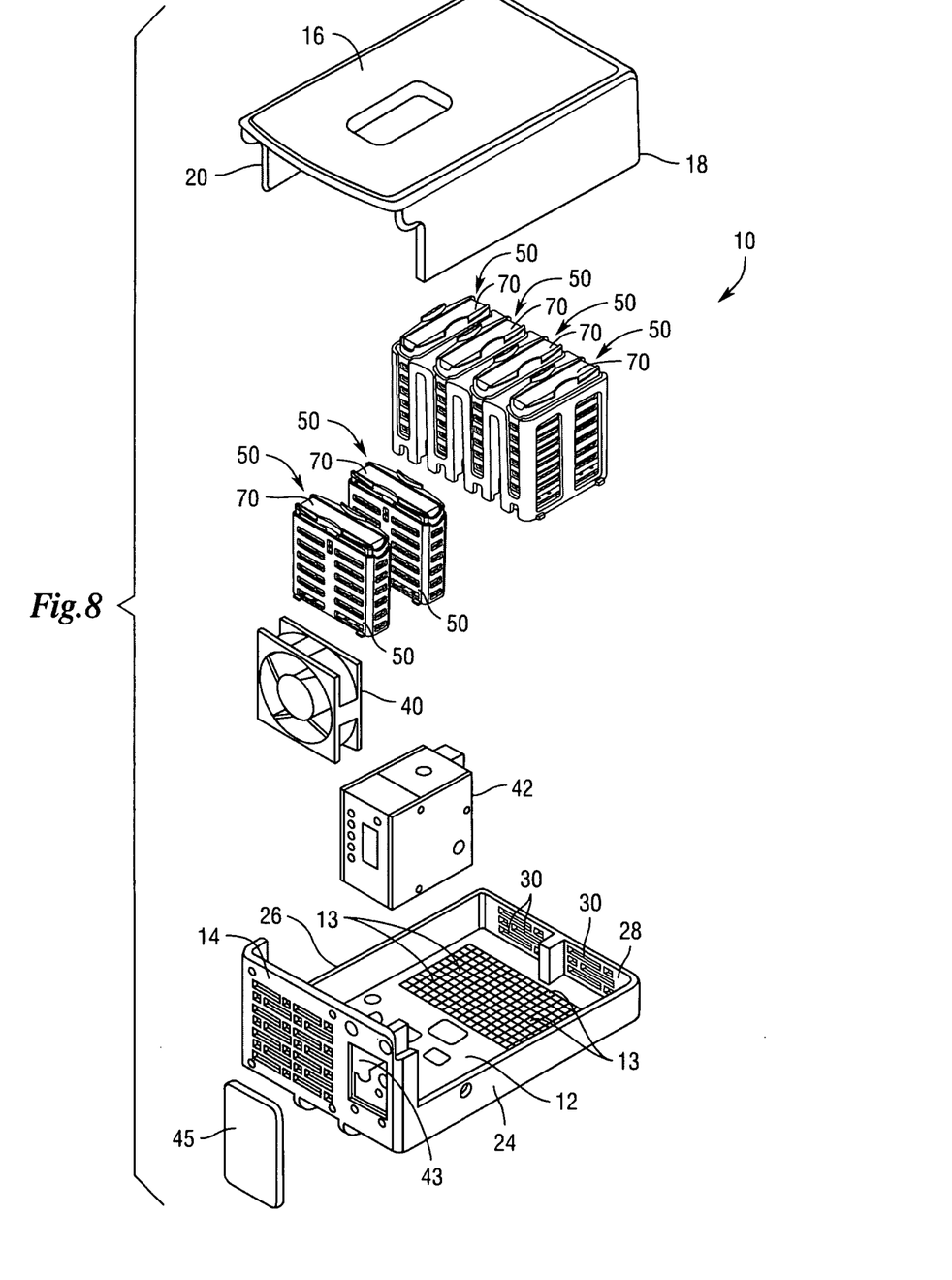
FIG. 8 is a perspective view of the aroma scent assembly of FIGS. 1 and 4 with the parts separated from each other to show details of construction.
Figure 9:
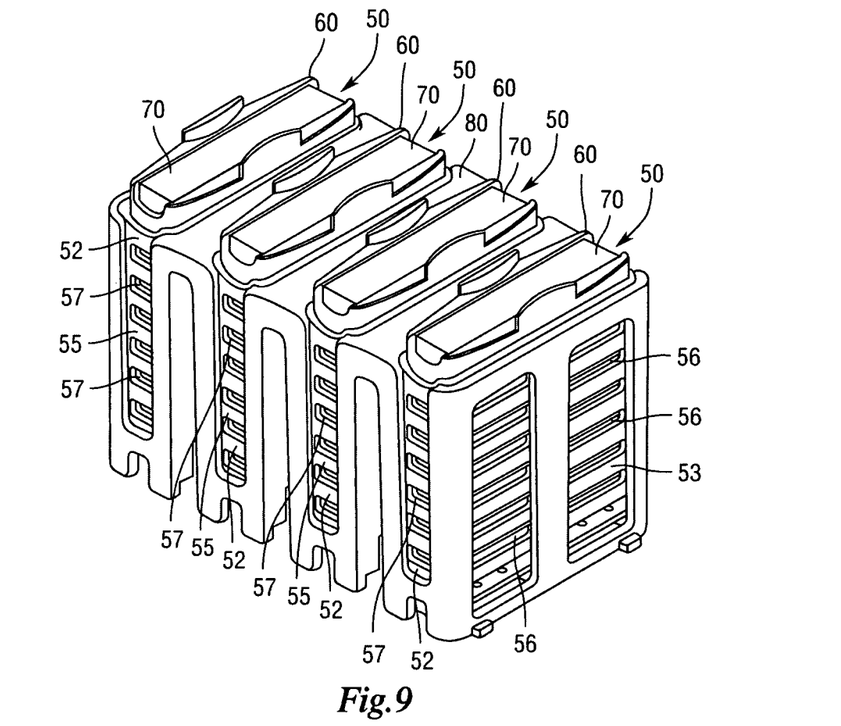
FIG. 9 is an enlarged perspective view of the aroma cartridge assembly of the aroma scent dispersing assembly of FIG. 1.
Figure 10:
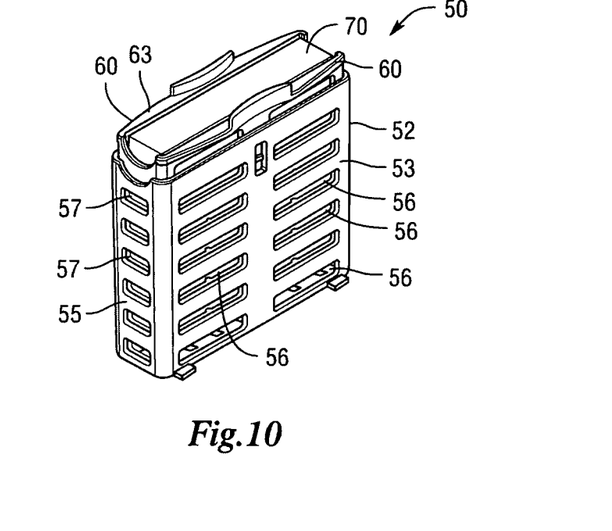
FIG. 10 is an enlarged perspective view of a holder and holster forming a shutter containing an aroma vapor wafer of the aroma cartridge assembly looking at the rear end wall of the shutter showing the array of parallel spaced passageways therethrough.

Disposed within inner compartment 34 of the assembly 10 is motor driven forced air fan assembly 40 suitably secured to and supported on base member 12. Supported also on base member 12 in compartment 34 is a control assembly 42 connected with the fan accessible 40. As shown in FIG. 8, the control assembly 42 has front arranged actuator switches accessible to a user through an opening 43 in the front end wall 14, the opening 43 enclosed by a selectively removable cover 45. The control assembly 42 is of any well-known construction and readily available as a shelf item. Included within the control assembly 42 may be a programmable timer, not shown, but also of well-known design, the programmable timer available to a user for selectively turning the motor drive fan 40 on and off at desired times throughout any day of the week.

Figure 13:
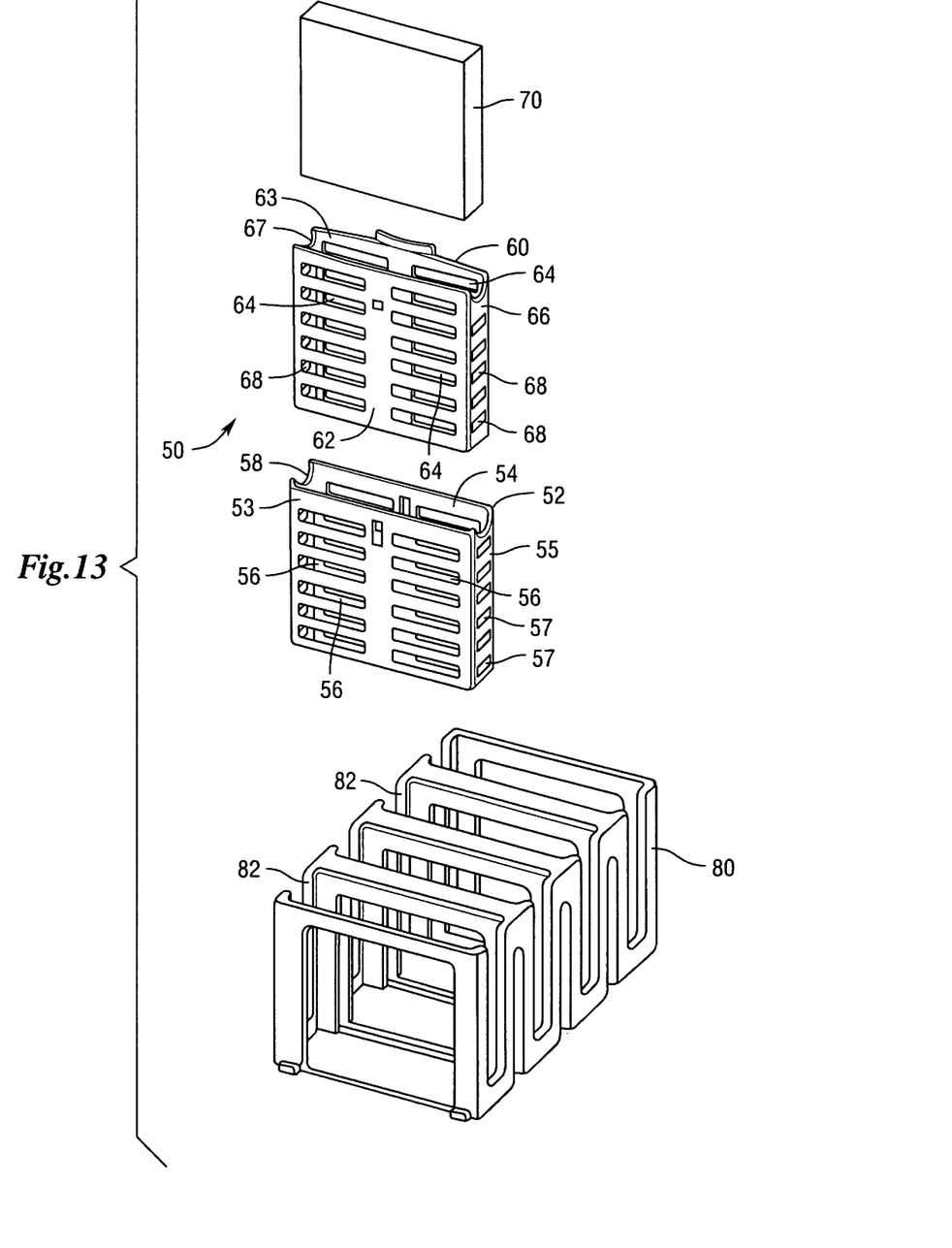
FIG. 13 is an exploded perspective view of the aroma cartridge assembly of the aroma scent dispersing assembly of FIG. 1 showing details of construction of the holder, holster and chassis.
Figure 14:
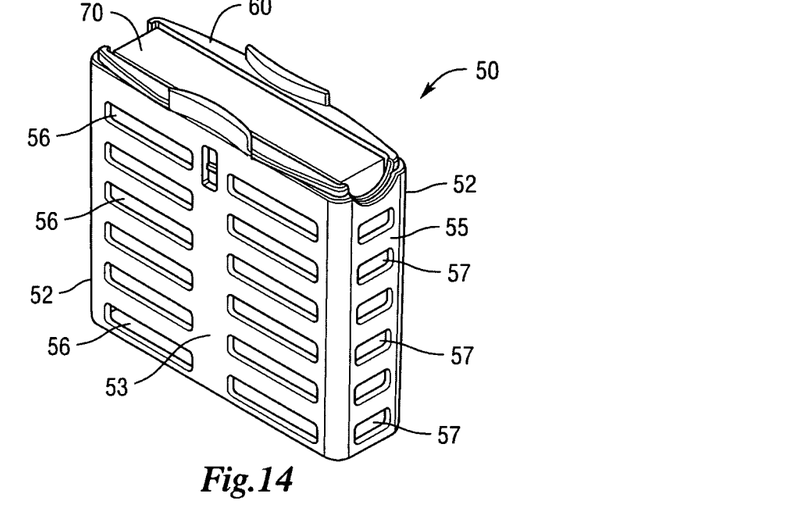
FIGS. 14 and 15 are enlarged perspective views of the holder and holster of the aroma cartridge assembly of the aroma dispersing assembly of FIG. 1 showing the relative positioning of the holster with respect to the holder showing in FIG. 14 the slots of the side walls of the holder and openings of the side walls of the holster closed with respect to each other and end wall apertures of the holder and openings of the end wall of the holster closed with respect to each other and showing in FIG. 15 the same holster slots and apertures fully open with respect to the holster apertures and openings respectively.
Figure 15:
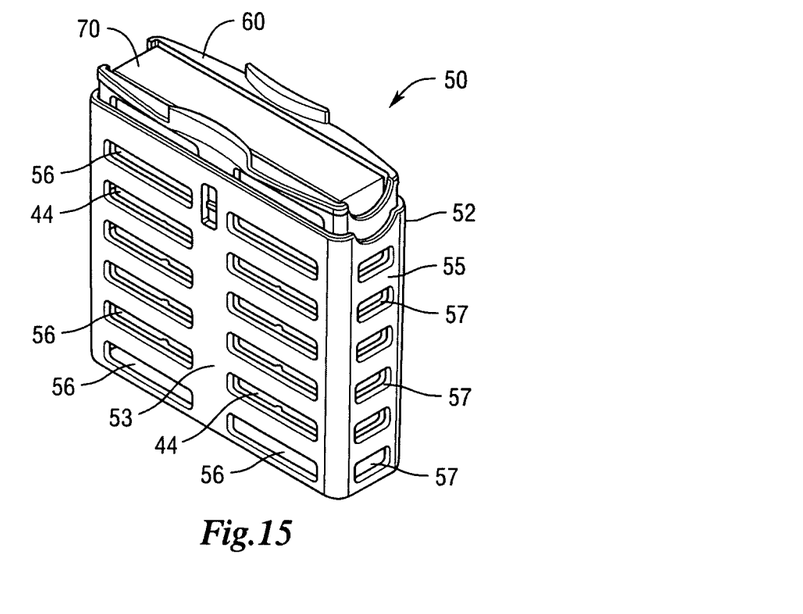
Figure 16:
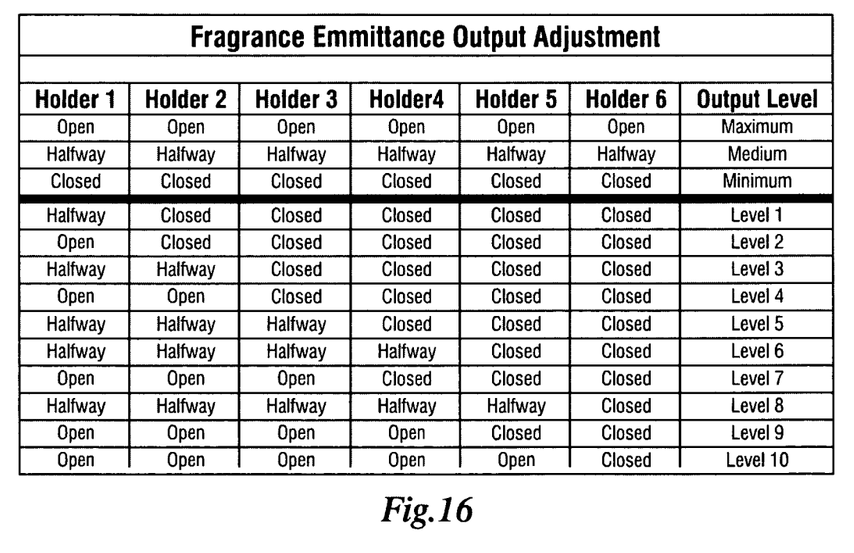
FIG. 16 is a representation of the fragrance emittance levels of the aroma scent dispersed from the aroma scent dispersing assembly of FIG. 1 based on the relative position of the holder and holster of the shutter of the vapor dispensing cartridge assembly between full opening of the holder side wall slots and holster side wall openings to the full closing thereof with respect to each other and full opening of the holder end wall apertures and holster end wall passageways and full closing thereof with respect to each other.

Arranged within the compartment 34 are a series of vapor dispersing cartridge assemblies 50, six shown with more or less being arranged as desired. One of the vapor dispersing cartridge assemblies 50 will be described with it being understood that the description thereof applies to each of the assemblies 50. As clearly shown in FIGS. 5, 8, 9, 10, 13, and 14, each vapor dispersing assembly 50 includes generally an open top box-shaped holder 52 having spaced side walls 53 and 54 defining an array of generally parallel slots 56 therethrough and spaced generally parallel front and back end walls 55 and 58 each defining an array of generally parallel end wall apertures 57 therethrough. Slidably received within and supported by the holder 52 is an open top, box-shaped holster 60, clearly shown in FIG. 13, having spaced side walls 62 and 63 defining an array of generally parallel openings 64 therethrough and opposite end walls 66 and 67 defining an array of generally parallel passageways 68 therethrough, the holder 52 and holster 60 are shaped, sized, and constructed such that when the holster 60 is slidably arranged within the holder 52, the slots 56 of the side walls 53 and 54 of the holder 52 will align partially or completely with and be generally the same size as the parallel openings 64 of the side walls 66 and 67 of the holster 60. Similarly, when the holster 60 is within the holder 52, the generally parallel apertures 57 of the front and back end walls 55 and 56 of the holder 52 will align partially or completely with the generally parallel passageways 68 of the end walls 66 and 67 of the holster 60. The holster is sized and shaped to snugly receive and support an aroma vapor emitting source such as a wafer 70 which would be exposed to the stream of air generated by the motor driven fan 40 through the open tops of the holder 52 and holster 60 and through fully or partially aligned slots 56 of the side walls 53 and 54 of the holder 52 and openings 64 of the side walls 62 and 63 of the holster 50 and through the fully or partially aligned apertures 57 of the front and back end walls 55 and 58 of the holder 52 and the passageways 68 of the end walls 66 and 67 of the holster 60. The combination of each holder 52 and holster 60 would be in effect a shutter for monitoring, metering, regulating, or controlling of the amount of exposure of the aroma scent emitting wafer 70 to the flow stream of air generated by the motor driver fan 40. As shown in FIG. 14 the holster 60 is positioned such that slots 56 of the side walls 53 and 54 of the holder 52 and apertures 57 of the front and back side walls 55 and 58 are closed from and not aligned with the opening 64 of the side walls 62 and 63 of the holster 60 and the passageways 68 of the end walls 66 and 67 of the holster 60, respectively. FIG. 15 shows the holster 60 positioned with respect to the holder 52 such that the slots 56 and apertures 57 of the holder 52 are completely aligned with the openings 64 and passageways 68 of the holster 60, respectively. Partial alignment of the slots 56 and apertures 57 of the holder 52 with the openings 64 and passageways 68 of the holster 60 may be anywhere between complete alignment of the slots 55, apertures 57, openings 64 and passageways 66 and complete closing of the slots 55, apertures 57, openings 64 and passageways 68 to each other, and thus will provide metering, regulating, varying or controlling the degree or amount of exposure of the air flow or stream to the aroma vapor emitting source such as wafer 70. At all positions of the holster 60 and holder 52, the top of each wafer 70 will be exposed to the air flow or stream and thereby air dispersed through the opening 30 of the end wall defined by the end section 22 of the cover 16 and lower end wall section 28 and through the opening 13 of the base member 12. With the assembly 10 in the on mode, that is the motor driven fan 40 generating a flow of air through the assembly 10, there will always be an aroma scent dispersed to the ambient surroundings. By adjusting the positions of the holster 60 relative to the fixed holder 52 the scent concentration of dispersed air flow may be varied as desired. The scent levels or concentration could be anywhere between the lowest and highest settings, as desired. Numbering the aroma vapor dispensing cartridge assemblies 50 and calling them holder 1 through holder 6, FIG. 16 details the typical scent levels or concentration that could be achieved by positioning the holster 60 and holder 52 between open, halfway, and closed positions, meaning complete aligned, partially aligned or closing to each other slots 55, apertures 57, openings 64, and passageways 66 of the respective holster 60 and holder 52.

It is to be noted that positioning the holster 60 with respect to the holder 52 is simply achieved by removing cover 16 and urging the holster 60 upwardly or downwardly between the completely or partial alignment or closed relationship of the slots 55, apertures 57, openings 64 and passageways 68 of the respective holster 60 and holder 52.

Figure 4:
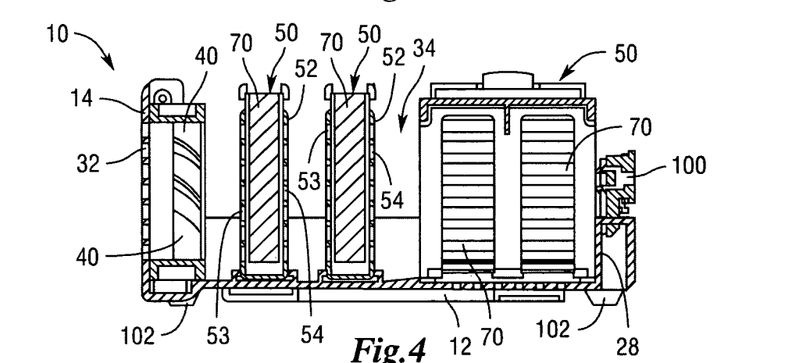
FIG. 4 is a view looking along the line IV-IV of FIG. 3 showing details of construction and attachment assembly on the lower section of the modified end wall.
Figure 5:
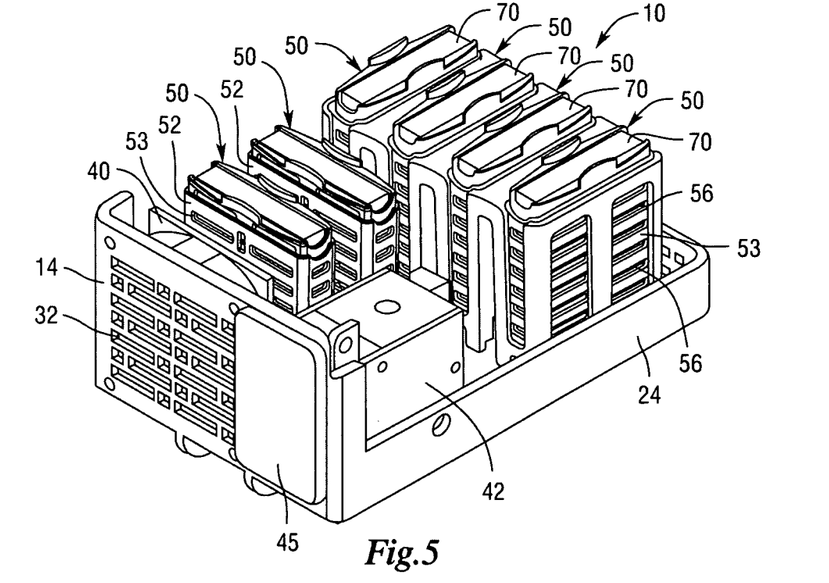
FIG. 5 is a perspective view of the aroma scent assembly of FIG. 1 with parts removed to show details of construction.
Figure 6:
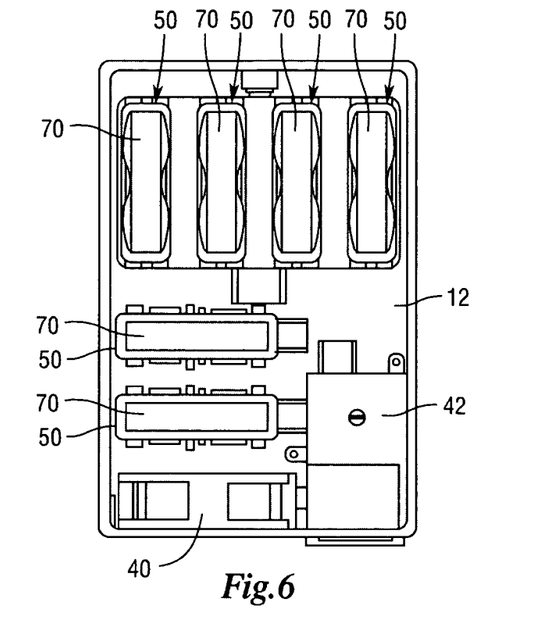
FIG. 6 is a top plan view of the aroma scent assembly of FIG. 5.
Figure 7:
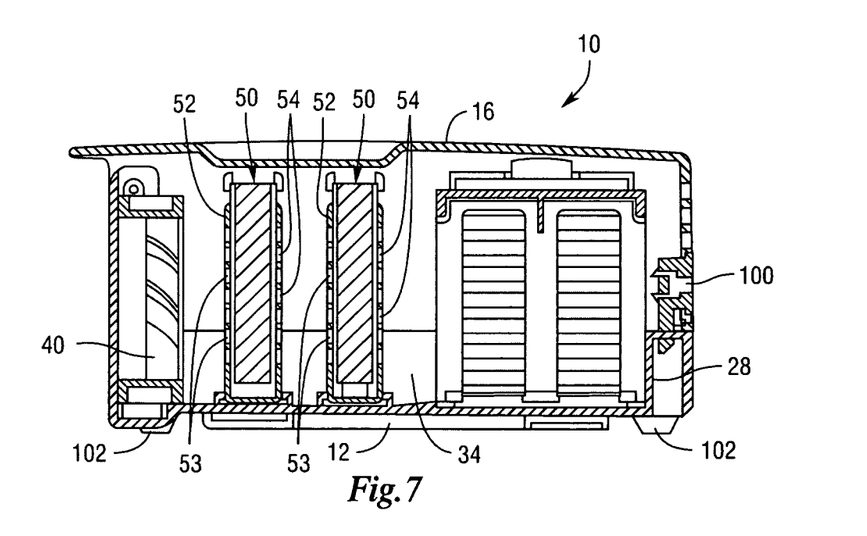
FIG. 7 is s sectional view of the aroma scent assembly of FIG. 1 showing details of construction.

The aroma scent dispersing assembly 10 also includes a chassis 80 formed of a series of generally U-shaped slots 82, four shown, secured by suitable attachments to this base member 12, the slots sized and shaped for snugly receiving the holders 52. As shown in FIGS. 4, 5 and 7, the holders 52 appearing at the right angles to the four parallel vapor dispersing cartridge assemblies 50, are secured directly on the base member 12 as clearly shown in FIG. 7 in a bracket, not numbered.

Figure 11:
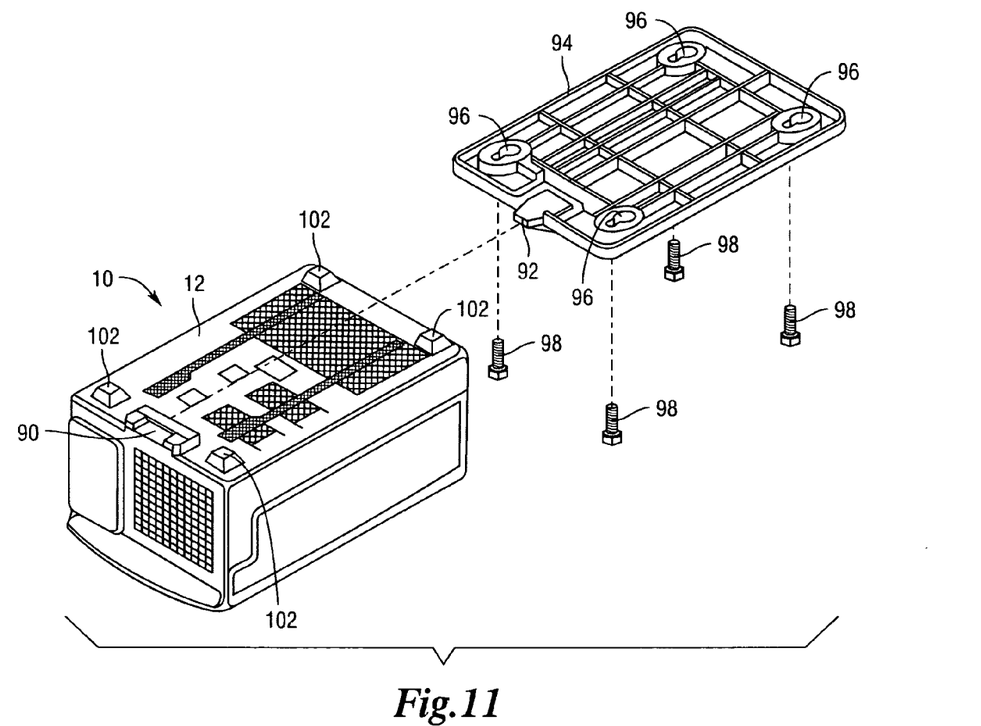
FIG. 11 is a perspective view of modified aroma cartridge assembly of FIG. 1 from the bottom thereof with parts broken away and show details of the construction.
Figure 12:
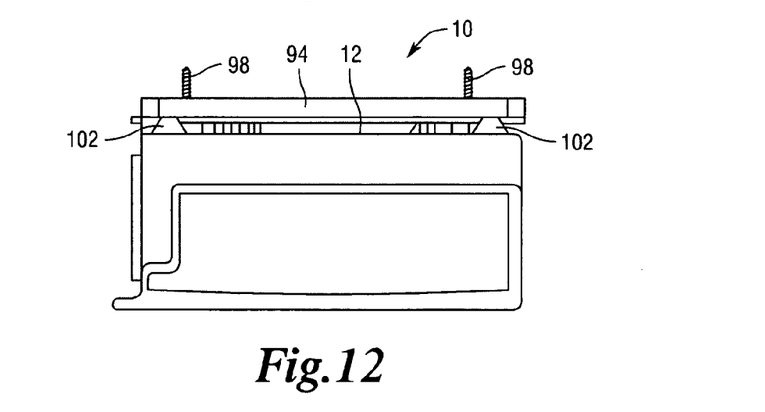
FIG. 12 is a side elevation view of the modified aroma scent assembly of FIG. 11.

The aroma scent dispersing assembly 10 may be sized so that it could be conveniently set on a floor surface, desk, table or such like. Mounting of the assembly 10 could also be on a wall or ceiling. FIGS. 11 and 12 show the base member 12 having on its outer front section a fixture or bracket 90 with the upper surface thereof raised to define a slot for snugly receiving the tab 92 of a mounting plate 94 and securing the mounting plate 94 to the assembly 10. The mounting plate 94 is provided with openings 96 for receiving and holding in place attachment screws 98. With the mounting plate 94 in place on the base member 12, the assembly 10 could be secured to a wall or ceiling surface by the attachment screws 98. The assembly 10 may also be secured to a wall surface by a vertically arranged attachment assembly 100 fixed to the lower wall section 28 as shown in FIG. 4. The assembly 10 may also be provided with suitably sized and shaped feet 102 fixed to the corner sections of the underside of base member 12, as shown in FIGS. 2, 2A, 7 and 11 for allowing the assembly 10 to be placed on a flat surface with the base member 12 above the flat surface for allowing clearance of the base member openings 13 and free discharge of scented air therethrough.

The aroma scent dispersing assembly 10 of my present invention allows metering, regulating, varying or controlling the amount of exposure of a vapor emitting source anywhere between a low and high scent level by simple adjustment of the interacting parts of an aroma dispersing cartridge assembly. Additionally, my aroma scent dispersing assembly may be suitably sized for allowing mounting on a wall, on the surface of a floor, table desk, or such like. My assembly may house any desired number of aroma scent dispersing cartridges, each of which would serve as a shutter for metering, regulating, varying, or controlling the amount of the vapor emitting source to the air stream flowing through the assembly. Various other modifications and advantages of the aroma scent dispersing assembly of any invention should be clearly understood by those skilled in the art.

While I have described certain present preferred embodiments of my invention, it is to be distinctly understood that the invention is not limited thereto buy may be otherwise embodied within the scope of the following claims.

What is claimed is:

1. An aroma scent dispersing assembly comprising:
   a housing having interconnected base member, selectively removable cover, opposite side walls, front and end walls, the housing defining an inner compartment; at least said end wall defining access openings therethrough;
   said base member defining opening therethrough;
   forced air means arranged within said compartment for selectively generating a flow of air from the front wall to the end wall through the access openings and to the base member and through the openings thereof;
   aroma vapor dispensing cartridge assembly means arranged in said compartment supported by said base member and defining apertures therethrough to expose the interior thereof to the flow of air from said forced air means for receiving and supporting a scented vapor emitting source exposed to the flow of air and for selectively metering and varying the amount of exposure of the vapor emitting source to the flow of air;
   said opening of said base member communicating with said aroma dispensing cartridge assembly means and the area outside the base member whereby flow of air will also be through the base member assembly openings;
   said aroma dispensing cartridge assembly means including a cartridge unit comprising in combination an open box-shaped holder having spaced side walls defining an array of slots therethrough and spaced front and back end walls defining an array of end wall apertures therethrough; a generally open top box-shaped holster sized and shaped to snugly receive and support a vapor emitting source slidably received within the holder, and having spaced side walls defining an array of openings alignable with said side wall slots of said holder, and opposite end walls defining an array of passageways therethrough alignable with said end wall apertures of said holder; said cartridge unit constructed and arranged such that said holster is selectively slidable in said holder between positions partially or completely aligning the side wall slots and end wall apertures of said holder with the side wall openings and end wall passageways of said holster, respectively, to position closing the side wall slots and end wall apertures from said holder side wall openings and end wall passageways of said holster; and whereby the flow of air will be over the top of the holster at all positions of the holder and the holster will, engage the interior of the holster when the side wall slots and end wall apertures and side wall openings and end wall passageways are aligned with each other and will bypass the interior of the holster when the side wall slots and end wall apertures and side wall openings and end wall passageways are completely closed with respect to each other; and
   including spaced feet member means fixed to the underside of said base member arranged for allowing the scent dispersing assembly to be placed on a generally flat surfaces with the base member above the flat surface for allowing clearance of the base member openings and free discharge of scented air therethrough.

2. The aroma scent dispersing assembly as set forth in claim 1 wherein the array of slots of said holder are generally parallel to each other and array of end wall apertures of said holder are generally parallel to each other; and wherein the array of openings of said holster are generally parallel to each other and the array of passageways of said holster are generally parallel to each other.

3. The aroma scent dispersing assembly as set forth in claim 1 wherein said aroma dispersing cartridge means includes a plurality of said cartridge units arranged within said compartment spaced from one another.

4. The aroma dispersing assembly as set forth in claim 3 wherein adjacent said cartridge units are spaced generally parallel to each other.

5. The aroma scent dispersing assembly as set forth in claim 1 wherein said forced air means is a selectively operable variable speed motor driven fan.

6. The aroma scent dispersing assembly as set forth in claim 1 wherein said holster is shaped and sized to snugly receive and support a scented vapor emitting wafer.

7. The aroma scent dispersing assembly as set forth in claim 5 wherein said variable speed motor driven fan is operatively coupled with a selectively variable control means for varying the speed of the fan.

8. The aroma scent dispersing assembly as set forth in claim 5 wherein said forced air means includes a programmable timing means for selectively turning the motor driving fan on and off at desired times.

9. The aroma scent dispersing assembly as set forth in claim 1 wherein said front wall defines openings communicating with said forced air means and the area outside of the front wall.

10. The aroma scent dispensing assembly as set forth in claim 1 includes attachment means fixed to the end wall for securing the aroma scent dispersing assembly to a generally flat vertical surface.

11. The aroma scent dispersing assembly as set forth in claim 1
   including a selectively removable support plate means fixed to the base member for securing the aroma scent dispersing assembly to a generally flat surface.

12. The aroma scent dispersing assembly as set forth in claim 1 wherein said selectively removable cover has side and flaps end sections both of which, when said cover is in place, form parts of the side walls and the end wall of said housing.

13. The aroma scent dispersing assembly as set forth in claim 1 including a chassis means secured to said base member and shaped and sized for selectively snugly removably supporting said aroma scent dispersing cartridge assembly means on said base member.

14. An aroma scent dispersing assembly comprising:

a housing including an elongated base member; an upper disperser cover; spaced apart front and back walls each defining access openings; and spaced apart side walls joined with the front and back wall and base member;

said base member; front and back walls, and side walls defining an inner compartment;

motor driven forced air means within the compartment supported by said front wall and base member for generating a flow of air between the base member, the access opening of the front end wall and through the access openings of the back wall;

a generally box-shaped aroma vapor dispensing cartridge assembly means within the compartment for selectively removably receiving a scented vapor emitting source exposed to the flow of air and for selectively metering the amount of exposure of the vapor emitting source to the flow of air;

said aroma dispensing cartridge assembly means including a cartridge unit comprising in combination an open box-shaped holder having spaced side walls defining an array of slots therethrough and spaced front and back end walls defining an array of end wall apertures therethrough; a generally open top box-shaped holster sized and shaped to snugly receive and support a vapor emitting source slidably received within the holder, and having spaced side walls defining an array of openings alignable with said side wall slots of said holder, and opposite end walls defining an array of passageways therethrough alignable with said end wall apertures of said holder; said cartridge unit constructed and arranged such that said holster is selectively slidable in said holder between positions partially or completely aligning the side wall slots and end wall apertures of said holder with the side wall openings and end wall passageways of said holster, respectively, to position closing the side wall slots and end wall apertures from said holder side wall openings and end wall passageways of said holster; and whereby the flow of air will be over the top of the holster at all positions of the holder and the holster will, engage the interior of the holster when the side wall slots and end wall apertures and end wall passageways are aligned with each other and will bypass the interior of the holster when the side wall slots and end wall apertures and side wall openings and end wall passageways are completely closed with respect to each other, said base member defining openings therethrough communicating with said aroma dispensing cartridge assembly means and the area outside the base member whereby the flow of air will also be through the base member openings and the access openings of said back wall;

including spaced feet member means fixed to the underside of said base member arranged for allowing the scent dispersing assembly to be placed on generally flat surfaces with the base member above the flat surface for allowing clearance of the base member openings and free discharge of scented air therethrough.

15. The aroma scent dispersing assembly as set forth in claim 14 including chassis means secured to said base member and shaped an sized for selectively removably supporting said aroma dispensing cartridge assembly means on said base member.

16. The aroma scent dispersing assembly as set forth on claim 14 including a plurality of said cartridge assembly means arranged within said compartment spaced from one another and wherein adjacent cartridge assembly means are spaced parallel to each other.

17. The aroma scent dispersing assembly as set forth in claim 14 wherein said motor driven forced air means include a variable speed selectively operable motor operatively coupled with a variable control means.

18. The aroma scent dispersing assembly as set forth in claim 14 including attachment means on either or both base members and/or back wall for selectively securing the aroma scent dispersing assembly on horizontal or vertical surfaces.

\* \* \* \* \*